(12) United States Patent
Pfaff

(10) Patent No.: US 8,574,497 B2
(45) Date of Patent: Nov. 5, 2013

(54) SEPARATOR AND SEPARATION STRIP

(76) Inventor: Dieter Pfaff, Neuberg an der Donau (DE)

( * ) Notice: Subject to any disclaimer, the term of this patent is extended or adjusted under 35 U.S.C. 154(b) by 1005 days.

(21) Appl. No.: 12/300,913

(22) PCT Filed: May 16, 2007

(86) PCT No.: PCT/EP2007/004390
§ 371 (c)(1),
(2), (4) Date: Apr. 27, 2009

(87) PCT Pub. No.: WO2007/131793
PCT Pub. Date: Nov. 22, 2007

(65) Prior Publication Data
US 2009/0321330 A1    Dec. 31, 2009

(30) Foreign Application Priority Data

May 16, 2006   (DE) .................... 20 2006 007 817 U

(51) Int. Cl.
*G01N 33/49* (2006.01)
*G01N 31/20* (2006.01)
*B01D 35/30* (2006.01)

(52) U.S. Cl.
USPC ............ 422/68.1; 422/50; 422/527; 210/236; 210/244; 210/455; 210/473; 436/16

(58) Field of Classification Search
USPC .................. 422/50, 401, 408, 430, 68.1, 527; 436/8, 16; 600/573, 584
See application file for complete search history.

(56) References Cited

U.S. PATENT DOCUMENTS

| | | | | |
|---|---|---|---|---|
| 4,065,263 | A | * | 12/1977 | Woodbridge, III ........... 422/427 |
| 4,288,228 | A | * | 9/1981 | Oberhardt ..................... 436/178 |
| 5,114,678 | A | * | 5/1992 | Crawford et al. ............. 422/565 |
| 6,555,390 | B2 | * | 4/2003 | Chandler ...................... 436/518 |
| 7,056,475 | B2 | * | 6/2006 | Lum et al. ..................... 422/505 |
| 2005/0106552 | A1 | | 5/2005 | Ikeda |
| 2006/0034728 | A1 | * | 2/2006 | Kloepfer et al. ............. 422/68.1 |

FOREIGN PATENT DOCUMENTS

| | | |
|---|---|---|
| DE | 3130749 | 3/1983 |
| DE | 202006007817 | 7/2006 |
| EP | 0278677 | 7/1992 |
| WO | WO 9303673 | 3/1993 |

* cited by examiner

*Primary Examiner* — Katherine Zalasky
(74) *Attorney, Agent, or Firm* — O'Shea Getz P.C.

(57) ABSTRACT

A separator (1*a*) under the invention for the taking of blood serum or blood plasma contained in a blood sample from a separating strip comprises a top part (3), a bottom part (4) and a joint (5). Said top part (3) and bottom part (4) are linked by the joint (5) in a pivoting way. Bottom part (4) is designed to support the separating strip. At least one nose (7*a*, 7*b*) is provided at the bottom part (4) and/or underside of top part (3) which can exert local pressure on the separating strip once top part (3) and bottom part (4) are folded together thus pressing blood serum or blood plasma out of the rear end of the separating strip.

20 Claims, 15 Drawing Sheets

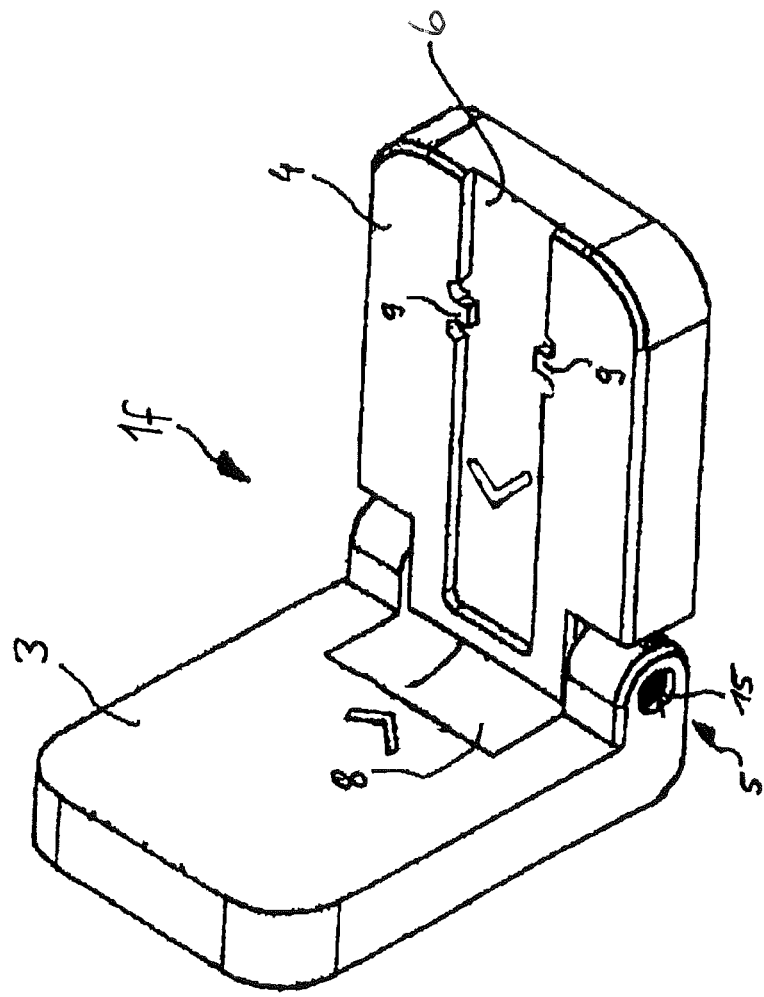
FIG.. 1F

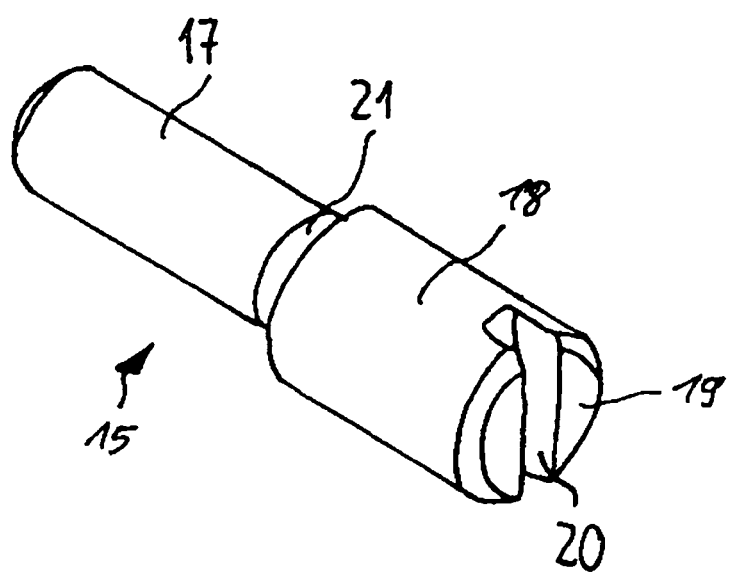
FIG.. 10

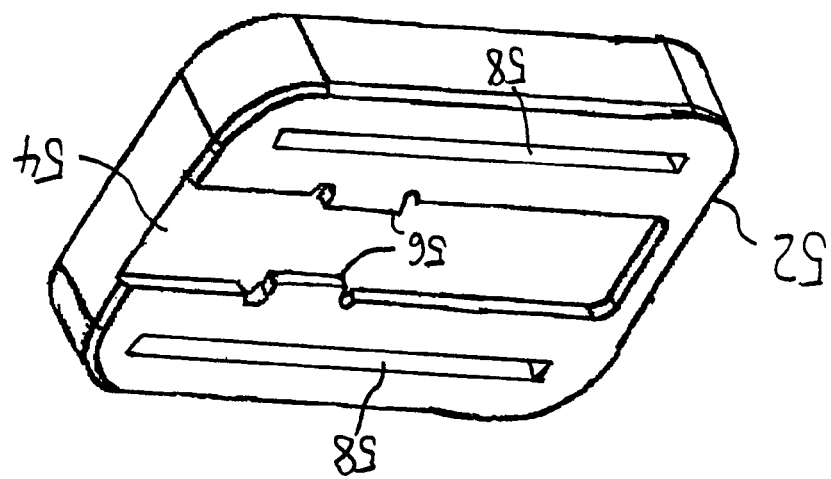
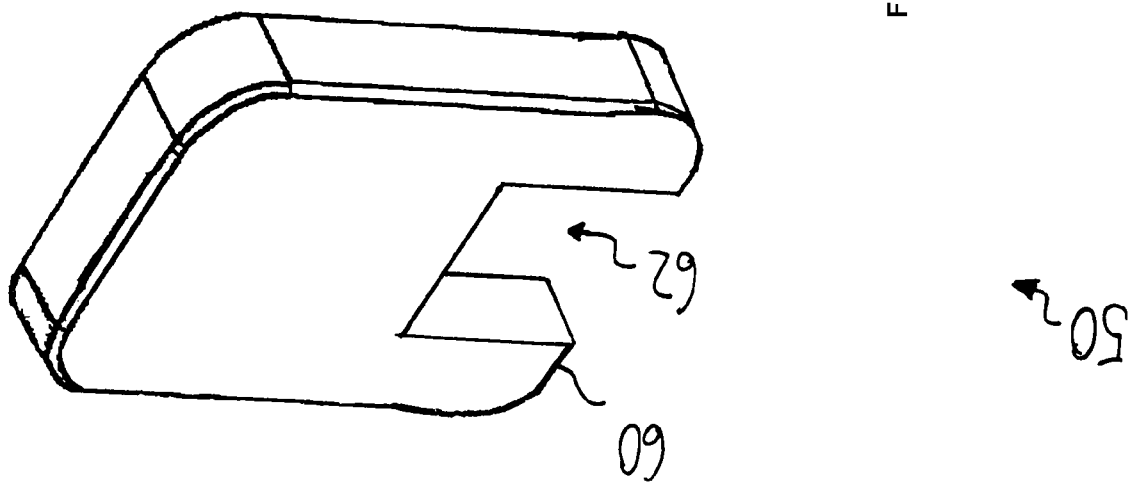
FIG. 11

SEPARATOR AND SEPARATION STRIP

This application is entitled to the benefit of, and incorporates by reference essential subject matter disclosed in PCT Application No. PCT/EP2007/004390 filed on May 16, 2007 which claims priority to German Application No. 20 2006 007 817.7 filed May 16, 2006.

BACKGROUND OF THE INVENTION

1. Technical Field

The invention relates to a separator and a separating strip for the separation of blood serum or blood plasma contained in a blood sample.

2. Background Information

From WO 2003/073095, we know of a separating strip for the separation of blood serum contained in a blood sample. It is hereby necessary to press the blood serum out of the separating strip, using fingers or fingernails, for instance. This is unpractical and bears the risk of damage to the separation test strips and blood serum contamination.

The present invention has the goal of providing both a device and a procedure to easily separate a defined quantity of blood serum or blood plasma without deteriorating the separation test strip or contaminating the blood serum or blood plasma.

SUMMARY OF THE INVENTION

This task is solved by the invention both with a separator for the taking of blood serum or blood plasma from a separating strip and with a separating strip for the separation of blood serum or blood plasma contained in a blood sample by means of a separator according to the independent claims.

A separator under the invention for the taking of blood serum or blood plasma contained in a blood sample from a separating strip comprises a top part, a bottom part and a joint which links the top part and bottom part together in a pivoting way so that the separator can be folded open and closed, wherein the underside of the top part and top section of the bottom part come into contact with each other at least in some areas in said folded-closed condition. The bottom part can support a separating strip which is inserted on the bottom part or pushed into an indentation provided in the bottom part for this purpose. The bottom part and/or the underside of the top part have at least one nose which can apply a defined local pressure on the inserted separating strip once the top part and bottom part are folded together. Blood serum or blood plasma is pressed out and can thus escape from the rear end of the separating strip whenever the separating strip is moved or only partially pulled out.

According to a basic idea of the invention, such a separator can exert a defined local pressure on the separating strip, and moving or at least partially pulling the separating strip out of the separator will be a simple way of taking the blood serum or blood plasma from the separating strip without touching or damaging it. The separator under the invention can therefore replace expensive special separating equipment.

A first embodiment of the separator under the invention provides exactly one nose in the separator exerting local pressure on the separating strip. Said nose may be provided at the underside of the top part, on the top of the bottom part or at the indentation, in particular on the floor of the indentation.

In a simple embodiment of the separator, the bottom part has an indentation into which the separating strip can be pushed and pulled out again. Such an indentation is able to exactly define the separating strip position inside the separator thus allowing a defined quantity of blood serum or blood plasma to be taken from the separating strip in a particularly reliable way. Instead of such an indentation, guide elements can be provided, including guide pins or guide bars or rails on the top of the bottom part which will enable the separating strip to be pushed in and pulled out in a similar way.

In another embodiment of the separator, a first nose is provided on the underside of the top part and a second nose on the floor of the indentation which will interact with each other once the separator is folded closed, exerting special pressure on the same area of the separating strip but from opposite sides. This allows for a good concentration of local pressure, and such a separator will therefore take a defined quantity of blood serum or blood plasma from the separating strip in a particularly reliable way.

Instead of the embodiment with two noses acting against each other, alternately one nose and an indentation opposite the nose in order to press the blood serum or blood plasma off the inserted separating strip can be provided.

If at least one nose is designed as a barrier, the separating strip can be moved and shifted in relation to the separator in a particularly advantageous way without any deterioration.

An especially good pull effect can be achieved if at least one of the noses runs transversally to the longitudinal direction of the indentation. As the pressure is exerted here almost over the entire width of the separating strip, the blood serum or blood plasma can be pressed out of the separating strip in a particularly efficient and uniform way.

In another embodiment, at least one nose is equipped with two legs arranged like an arrow, the vertex of the arrow either facing the direction in which the separating strip is pulled out of the separator, or the joint. The blood serum or blood plasma will therefore be concentrated in the central area of the separating strip when the latter is pulled out, and pressed out of the separating strip in a centerline position.

In another embodiment, at least one nose is shaped like a bow, the bow opening facing the direction in which the separating strip is pulled out of the separator. The blood serum or blood plasma will therefore be concentrated in the central area of the separating strip when the latter is pulled out, and pressed out of the separating strip in a centerline position.

In an alternative embodiment, at least one nose is shaped like a roller or roll. The blood serum or blood plasma can thus be pressed out of the separating strip without damage. The separating strip can be pulled out of the separator in a particularly easy way, and any breakage of the separating strip can be avoided by too strong pulling motions. In this design, the roller or roll especially rotate around an axle inserted in the top part and/or the bottom part.

In another embodiment of the invention, at least one drive motor for the roller or roll is provided which automatically moves and shifts the inserted separating strip.

According to another embodiment of the invention, the top part which is placed near the one nose at least has an opening allowing the blood serum or blood plasma taken from the separating strip to sit on the bottom part of the separator, thus allowing access to it through said opening once the separator is folded closed. This will further enhance the user-friendliness of the separator, as the blood serum or blood plasma pressed out of the separating strip can be especially easily taken, using a pipette, for instance, without having to unfold the separator first.

In another embodiment of the invention, the one nose at least is made from an elastic material, in particular from rubber. Alternatively, the one nose can be designed at least as a metal tongue which will be elastic due to its structural design. This results in the separating strip being pressed together with sufficient force to reliably press the blood serum or blood plasma out of the separating strip, on the one hand, and in the prevention of damage of the separating strip by the elasticity of the one nose at least during operation, if separating strip is pulled out of the separator too fast or press together the top part and bottom part too heavily, on the other hand.

Both the top part and bottom part can be manufactured from a durable and impact-resistant material which can easily be disinfected, such as a suitable plastic material or metal.

In another embodiment of the invention, the joint is formed by drilled bores in the top and bottom part through which a pivot pin is inserted. The pivot pin can also be manufactured from suitable material such as metal or plastic. The pivot pin can be provided with a slot of an oblong or cross shape on at least one head end into which the pivot pin may easily be inserted and in order to insert or turn it into the drilled bores by means of a screwdriver.

In another embodiment, both the top part and the bottom part are provided with permanent magnets which are arranged so that they will face each other in the folded-closed condition and attract each other, thus holding together the top part and bottom part due to their force of magnetic attraction. This allows for the compression of top part and bottom part with an exactly defined force, thus exerting a defined force on the separating strip which is sufficiently high to press the blood serum or blood plasma out of the separating strip without damaging the separating strip.

In an alternative embodiment, either the top part or the bottom part is only provided with a permanent magnet. The other part which is not provided with a permanent magnet, is made of metal or equipped with magnetic metal platelets. The permanent magnets and the metal platelets are arranged so that they will face each other in the folded-closed condition, thus holding together the top part and bottom part due to the force of magnetic attraction. This embodiment is inexpensive as a lower number of permanent magnets is used.

The invention also relates to a separator for the taking of blood serum or blood plasma contained in a blood sample from a separating strip including a bottom part (52) and a top part which can be moved in relation to the bottom part. The bottom part is designed to support a separating strip which is inserted on the bottom part or pushed into an indentation provided in the bottom part for this purpose. At least one nose is provided in the underside of the top part to exert a defined local pressure on the inserted separating strip. When the top part is moved in the direction of the front end of the inserted separating strip, the blood serum or blood plasma is pressed out of the front end and thus escapes from the separating strip.

According to a basic idea of the invention, such a separator will apply a defined local pressure on the separating strip, and moving the top part against the bottom part will make the nose affect the separating strip, thus in a simple way taking blood serum or blood plasma from the separating strip without touching or damaging it.

By arranging and moving the top part at a defined distance from the bottom part, the nose will cause a constant pressure to the separating strip and the blood serum or blood plasma will be pressed out of the separating strip with constant efficiency.

In a first embodiment of the separator according to the invention, the nose is a roller which results in a careful treatment of the separating strip, prevents it from damage and ensures especially efficient pressing out of blood serum or blood plasma. The roller or roll will especially rotate around an axle inserted in the top part.

According to another embodiment of the invention, an electrical drive motor can be provided for the roller, the motor being integrated into the top part, for instance, to press the blood serum or blood plasma out of the separating strip automatically and at a specified speed and thus even more reliably.

The moving mechanism shifting the top part against the bottom part may have any design. According to one, guide bars are provided on which the top part can be shifted against the bottom part, using gliders engaging into and running in the guide bars, for instance.

To ensure maximum shifting position of the top part against the bottom part, at least one limit stop can be provided. The latter may be provided by the end of the guide bar which marks a stop for a glider or gliding element.

According to another embodiment of the invention, the top part has an indentation which is arranged so that the blood serum or blood plasma escaping from the rear end of the separating strip becomes accessible once the top part has been shifted against the bottom part and the blood serum or blood plasma has emerged from the rear end of the separating strip by action of the nose. This indentation can especially be located in a central area of the rear end of the top part.

Instead of an indentation, the top part can be designed in a shorter version so that its end is arranged in the maximum shifting position in such a way as to enable access to be made to the blood serum or blood plasma which escapes from the rear end of the separating strip.

According to another embodiment of the invention, the indentation has at least one lug on at least one longitudinal side. Each longitudinal side may especially be provided with one lug.

In the pivoting version of the separator, the lug provides a narrow portion including a front and rear limit stop so that the separating strip can be shifted across the distance defined by the stops, thus pressing out a defined quantity of blood serum or blood plasma out of the separating strip through the at least one nose. This further enhances user-friendliness as the separating strip does not need to be fully pulled out of the separator, but only across a certain distance defined by the stops.

In the shifting version of the separator, the lug is preferably dimensioned so that it will engage into a corresponding opening of the separating strip, thus fixing the separating strip in or on to the bottom part.

In another embodiment, a chronometer unit with a signal transmitter is provided in the top part or bottom part. The chronometer unit measures a specified period and the signal transmitter will emit an optical or acoustical signal after expiry of this period. The chronometer unit may have control keys with which the required period can be manually set. The start of the period can be signaled to the chronometer unit by pressing a control key, by inserting a separating strip, which can be detected by means of a switch or sensor, in the case of the pivoting version of the separator by the folding together of the top and bottom part, which can be detected by means of a switch or sensor, in the case of the shifting version of the separator by placing the top part on the bottom part, which can be detected by means of a switch or sensor. The signal transmitter can be designed as a digital display with number characters which will start to light up or flash after expiry of the period. The signal transmitter can also be an LED or buzzer.

The invention also relates to a separating strip for the separation of blood serum or blood plasma contained in a blood sample by means of a separator. Such a separating strip is also called a getter, comprising a blood separating component, a retaining component for the covering and retaining of the blood separating component, a blood introducing section which is provided in a section covering the front section of the blood separating component, and an opening for blood-taking which is provided in a section covering the rear end of the blood separating component. On at least one longitudinal side, the separating strip has at least one narrow portion including a rear and a front limit stop so that the separating strip can be moved across the distance defined by the limit stops. The result is that the separating strip can be moved across the length defined by the distance of the front and rear limit stop and by the width of the lug at the longitudinal side of the indentation in the separating strip when said lug is provided at the longitudinal side of the indentation or a guide element provided on the separator. It is therefore not necessary to pull the separating strip fully out of the separator or fold the separator open in order to process the taken blood serum or blood plasma.

In an advantageous development of the separating strip, the limit stops of the separating strip narrow portion have the task to mark a stop for a lug in the bottom part, in particular for a lug on the side edge of the separator indentation.

In an advantageous development of the separating strip, the limit stops of the narrow portion have the task of fixing the separating strip against a fixing nose in the bottom part.

In a particularly advantageous embodiment, the separating strip is designed so that the blood sample can be introduced into the blood separating component through a blood introducing section, that the introduced blood sample can be separated by capillary action in such a way that the blood serum or blood plasma is collected in the front end of the blood separating component and the erythrocytes in the rear end of the blood separating component. This ensures that the blood serum or blood plasma will only be pressed out of the separating strip and separated for further processing, not the erythrocytes An especially simple and reliable embodiment of the separating strip comprises a rectangular narrow portion on at least one longitudinal side of the separating strip. Such a rectangular narrow portion can easily be manufactured by a suitable punching tool, and the distance between the front and rear limit stop of the narrow portion is exactly defined.

If the separating strip is provided with a side shaped like a semicircle or V, the blood serum or blood plasma can collect in the central area of the separating strip especially well and be pressed out of it in a centerline position.

The invention also relates to a procedure for the separation of blood serum or blood plasma contained in a blood sample by use of a separator according to the invention of the pivoting version and a separating strip according to the invention. The blood sample is applied to the blood insertion component of the separating strip at first. The separating strip is now inserted on to the bottom part, in particular into the indentation of the bottom part of the separator, and after expiry of a certain period, the top part and the bottom part of the separator are folded together and pressed against each other and the separating strip is pulled out in the direction of its rear end. The result is that the blood serum or blood plasma separated from the erythrocytes by capillary action before, is pressed in the direction of the rear end of the separating strip through at least one nose and escapes through the opening at the rear end of the separating strip.

The invention also relates to a procedure for the separation of blood serum or blood plasma contained in a blood sample by use of a separator according to the invention of the shifting version and a separating strip according to the invention. The separating strip is inserted on the bottom part, in particular into the indentation of the bottom part of the separator, and the blood sample is applied to the blood insertion component of the separating strip. The top part is placed on to the bottom part, and after expiry of a certain period, the top part is shifted against the bottom part. The result is that the blood serum or blood plasma separated from the erythrocytes by capillary action before, is pressed in the direction of the rear end of the separating strip and escapes through the opening at the rear end of the separating strip.

This procedure achieves an especially simple and reliable taking of blood serum or blood plasma from the separating strip without damaging the separating strip. All other characteristics, embodiments and advantages mentioned for the above separator and separating strip also apply to the separating procedure according to the invention.

A particularly advantageous embodiment makes use of a separator with an indentation which is provided with a lug on at least one longitudinal side, and of a separating strip which is provided with at least one narrow portion on one longitudinal side.

On the separator of the pivoting version, the separating strip is pulled out of the separator with its front end first until the one lug at least on the side wall of the indentation provided in the bottom part of the separator makes contact with the front end of the separating strip opening. The result is that the separating strip is shifted across a previously exactly defined length thus pressing a defined quantity of blood serum or blood plasma out of the separating strip.

In a particularly advantageous embodiment, the escaped blood serum or blood plasma is taken using a bulb making it thus directly available for further processing or analysis.

The invention is now described in detail using some examples of embodiments referring to the figures below.

BRIEF DESCRIPTION OF THE DRAWINGS

FIG. 1f shows an exploded view of a sixth separator according to the invention in its folded-open condition according to an example of embodiment;

FIG. 2a shows a sectional view of a first separating strip according to the invention according to an example of embodiment;

FIG. 2b shows a plan view of the first separating strip displayed in FIG. 2a;

FIG. 10 shows an exploded view of a pivot pin;

FIG. 11 shows an exploded view of a seventh separator under the invention, including a bottom part and top part removed from it, according to an example of embodiment;

DETAILED DESCRIPTION OF THE INVENTION

Figure 1A:
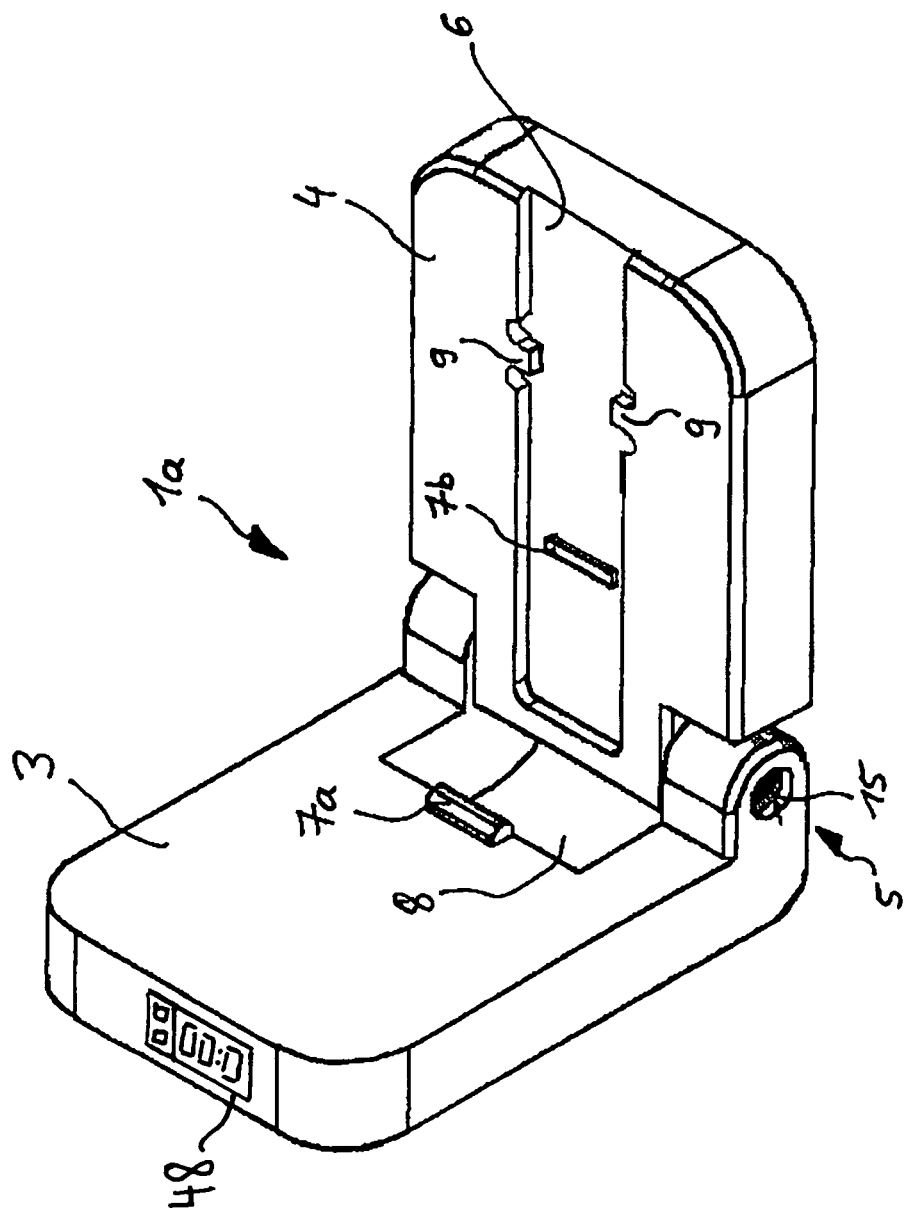
FIG. 1a shows an exploded view of a first separator according to the invention in its folded-open condition according to an example of embodiment.

FIG. 1a shows an exploded view of a first separator 1a according to the invention in its unfolded condition without any separating strip inserted.

The first separator 1a comprises a bottom part 4 and a top part 3, which is displayed in an almost vertical position to the bottom part 4. In its lower area, the top part 3 has articulated projections placed on top of part 3 in a rectangular position. These articulated projections and the stepped end section of bottom part 4 encompassed by these articulated projections, which is shown on the left of FIG. 1a, have drilled bores running through them through which a pivot pin 15 is inserted, thus forming the joint 5 around which the bottom part 4 and top part 3 can be pivoted and folded.

The material thickness and the dimensions of top part 3 and bottom part 4 are roughly the same. The edges of bottom part 4 facing the right side in FIG. 1a are rounded, which is also true for the edges of top part 3 shown in an upward direction in FIG. 1a. The side faces of top part 3 will therefore be roughly aligned with each other in the folded-closed condition.

As can be seen in FIG. 1a, top part 3 has an opening 8 near the joint so that the rear end of the top of bottom part 4 will be accessible from above when the first separator 1a is folded closed.

On the top of bottom part 4, there is an indentation 6 which is running across the top of bottom part 4 from the front to the rear, limited by side walls on the right and left, and open to the front. The side wall shown in the rear in FIG. 1a may also have an opening in order to allow better access for the taking of separated blood serum or blood plasma.

On the left and right side wall of indentation 6 there are some lugs 9 which are nose-shaped and opposed to each other, which protrude to the side of indentation 6, thus reducing its width in this area. The two nose-shaped lugs 9 are arranged in a front area of indentation 9 in this FIG. 1a, and they represent limit stops 9 for a separating strip which will be described in detail in the following.

On the top part 3, directly adjoining to the rectangular opening 8, there is a barrier-shaped nose 7a running transversally to indentation 6, and which is facing the front in FIG. 1a, therefore facing downwards when the first separator 1a is folded closed.

On the floor of indentation 6, in the rear area of indentation 6, there is another nose 7b which protrudes upwards in FIG. 1a out of indentation 6. This second nose 7b is arranged so that it interacts with the first nose 7a once the first separator 1a is folded closed. The second nose 7b is also barrier-shaped and running transversally to the longitudinal direction of indentation 6.

The noses 7a and 7b in FIG. 1a are only illustrations of examples and can have any design; one of the two noses may be of a larger width, or the noses can be of curved or rounded shapes, for instance.

In the top part 3, there is a chronometer unit 48 comprising a digital display and two control keys to the right of it in FIG. 1a. Using the chronometer unit, a period can be stopped which will be needed for the separation of blood serum or blood plasma from the erythrocytes by capillary action in the separating strip and its collection at the front end of the blood separating component near the opening for blood-taking. After expiry of this period, the separator 1a can be used to press out the blood serum or blood plasma from the separating strip.

The period can be manually set with the control keys. A period of approx. 0.5 minutes will need to be set for the blood sample from an adult, a period of approx. 1 minute for a blood sample from a newborn, and a period of 2 minutes for the blood sample from a premature baby, for instance.

The period starts with the introduction of a blood sample into the separating strip. The beginning of the measuring of time will be signalled to the chronometer unit 48 by pressing a control key on chronometer unit 48. Alternatively, the beginning of the measuring of time can also be specified as the moment of folding closed the top part 3 and bottom part 4 which will be detected by a switch or sensor not shown in FIG. 1a.

After expiry of the period, chronometer unit 48 can emit an optical or acoustical signal signalling that the separating strip can now be pulled back in order to press out the blood serum or blood plasma.

In the simplest embodiment of chronometer unit 48, the latter can be provided with an LED which starts to light up or flash after expiry of the period, and/or a buzzer generating a buzzing sound after expiry of the period, instead of a digital display.

Although chronometer unit 48 is only illustrated in the first separator 1a, it can also be integrated into any of the following separators 1b, 1c, 1d and 1e. A separate description of chronometer unit 48 referring to the separators 1b, 1c, 1d and 1e is dispensed with to avoid repetitions.

Figure 1B:
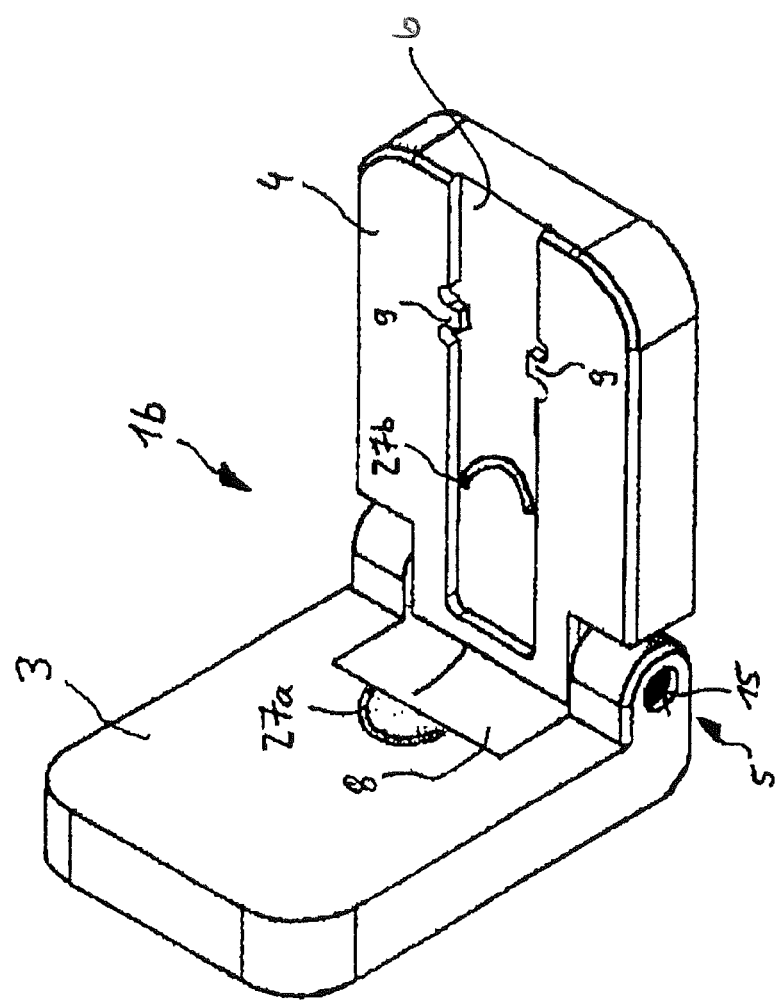
FIG. 1b shows an exploded view of a second separator according to the invention in its folded-open condition according to an example of embodiment.

FIG. 1b shows an exploded view of a second separator 1b under the invention according to a second embodiment in its unfolded condition without any separating strip inserted.

The second separator 1b is distinguished from the first separator 1a by having a third nose 27a shaped like a semicircle and a fourth nose 27b shaped like a semicircle instead of the first nose 7a and the second nose 7b. The semicircle openings of the third nose 27a and of the fourth nose 27b face the joint 5.

Figure 1C:
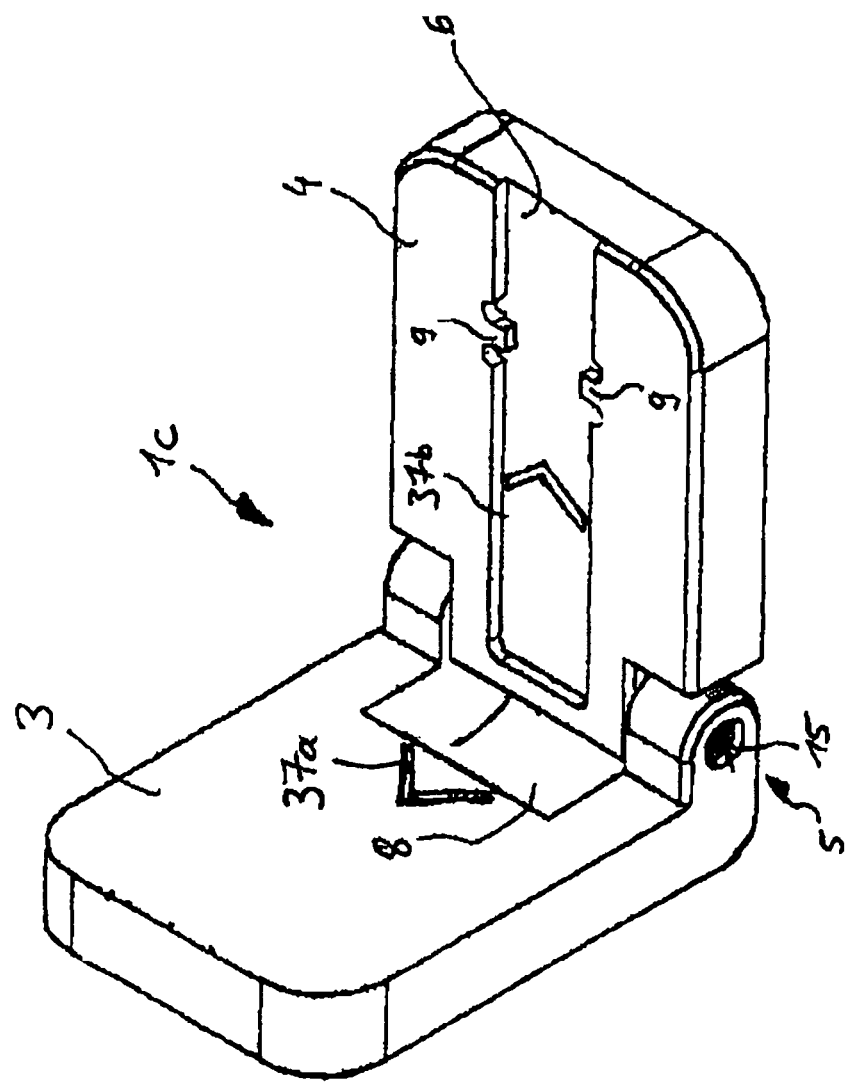
FIG. 1c shows an exploded view of a third separator according to the invention in its folded-open condition according to an example of embodiment.

FIG. 1c shows an exploded view of a third separator 1c according to a third embodiment in its unfolded condition without any separating strip inserted. The third separator 1c is distinguished from the first separator 1a by having, instead of the first nose 7a and the second nose 7b, a fifth nose 37a shaped like a V and a sixth nose 37b shaped like a V which are designed as legs of an isosceles triangle, the vertex of the triangle connecting the two legs facing away of joint 5.

Figure 1D:
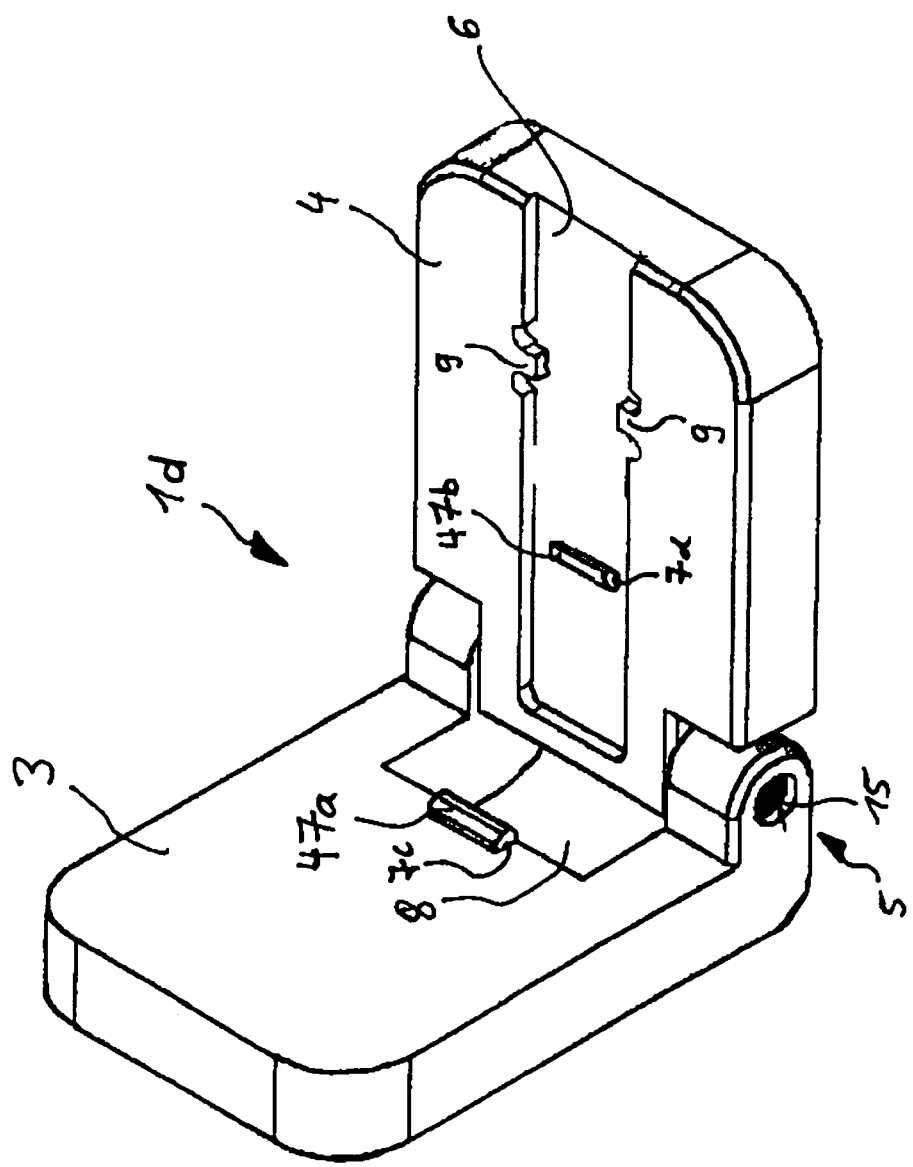
FIG. 1d shows an exploded view of a fourth separator according to the invention in its folded-open condition according to an example of embodiment.

FIG. 1d shows an exploded view of a fourth separator 1d according to a fourth embodiment in its unfolded condition without any separating strip inserted.

The fourth separator 1d is distinguished from the first separator 1a by having, instead of the first nose 7a and the second nose 7b, a first roller or roll 47a and a second roller or roll 47b. The provision of rollers 47a and 47b has the result that the separating strip can be moved and shifted requiring less force and thus easier.

The first roller 47a and a second roller 47b can be rotated around a first axle 7c and a second axle 7d which are approximately arranged at the height of top part 3 and of the top side of bottom part 4 and in particular in the top part 3 and the bottom part 4, these axles being oriented rectangular to the longitudinal direction of indentation 6 or the rotating direction of the separating strip respectively, so that they undergo rotary motion once the separating strip is forced to move or shift.

Alternatively, an electrical drive motor can be provided, which is not shown in FIG. 1d at least, which drives the rollers 47a and 47b during operation. This drive motor is preferably integrated into the top part 3 or the bottom part 4 of the fourth separator 1d. Both rollers 47a and 47b can be driven if a common electrical drive motor is provided either in top part 3 or bottom part 4, or one electrical drive motor can be provided for roller 47a in top part 3 and another for roller 47b in bottom part 4.

Figure 1E:
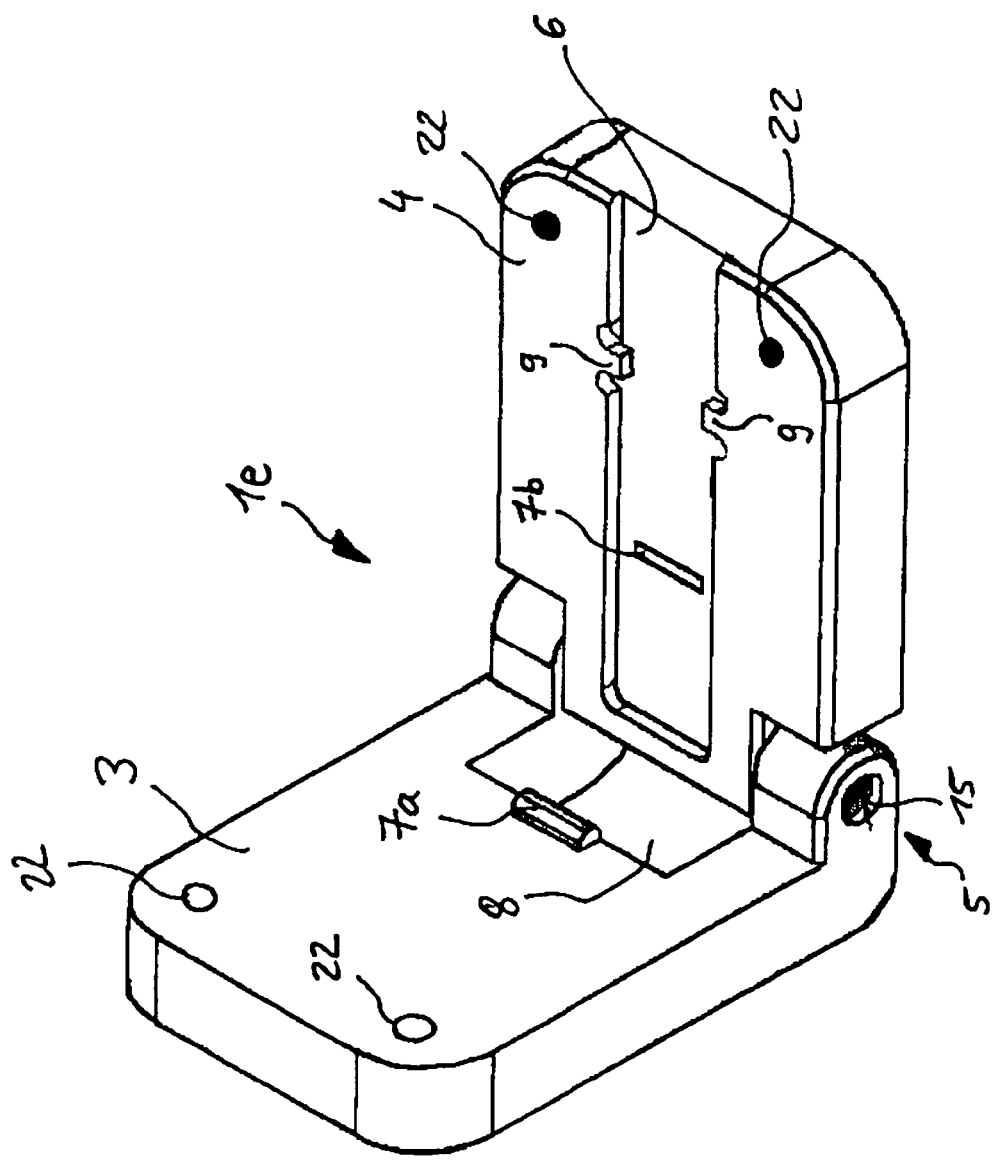
FIG. 1e shows an exploded view of a fifth separator according to the invention in its folded-open condition according to an example of embodiment.

FIG. 1e shows an exploded view of a fifth separator 1e according to a fifth embodiment in its unfolded condition without any separating strip inserted.

The fifth separator 1e is distinguished from the first separator 1a by the provision of permanent magnets 22 both in the rounded corners of top part 3 and rounded corners of bottom part 4. In the view of the example in FIG. 1e, these are of a circular cross-section and are arranged in such a way as to be facing each other when the fifth separator 1e is folded closed. The permanent magnets 22 of top part 3 and the permanent magnets 22 of bottom part 4 have an opposed magnetization so that they attract each other. When the fifth separator 1e is folded closed, a defined force will be applied between top part 3 and bottom part 4, which replaces manual compression of top part 3 and bottom part 4.

FIG. 1f shows an exploded view of a sixth separator 1f according to a sixth embodiment in its unfolded condition without any separating strip inserted.

The sixth separator 1f is distinguished from the third separator 1c by the V-shaped noses 38a and 38b being designed as legs of an isosceles triangle and the vertex of the triangle joining the two legs facing the joint 5.

Figure 2:
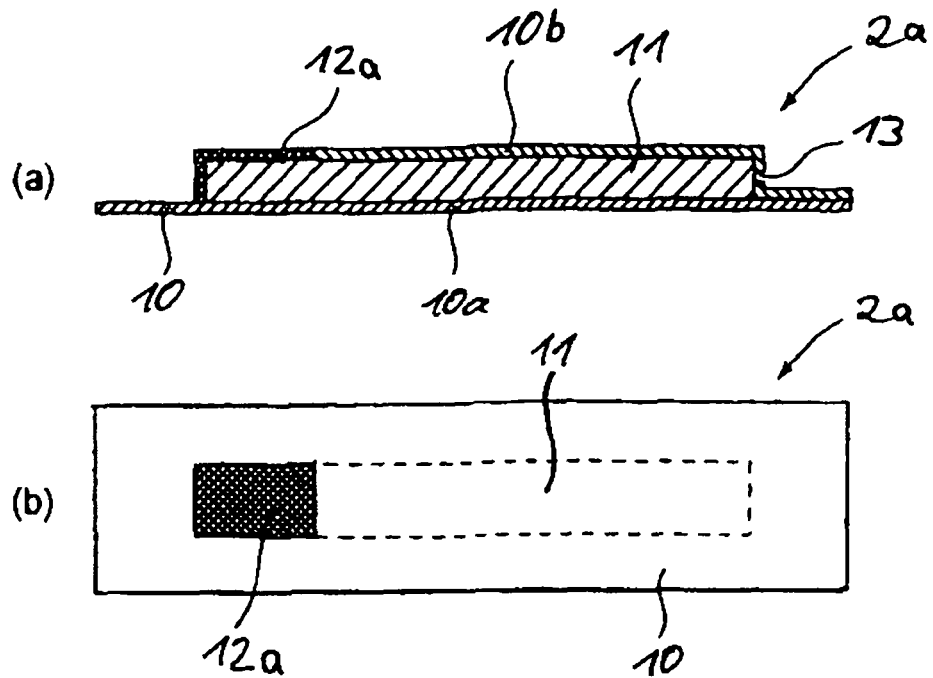

FIG. 2 shows a first separating strip 2a under the invention according to a first embodiment represented in a sectional view (FIG. 2a) and a plan view (FIG. 2b).

Said first separating strip 2a is designed for separating blood serum or blood plasma contained in a blood sample. The central area of FIG. 2a displays a blood separating component 11 which is encompassed by a retention component 10. Retaining component 10 comprises a bottom retaining component 10a and a top retaining component 10b which encompass the blood separating component 11. A first blood introducing section 12a is provided in the front section of the top retaining component 10b shown in FIG. 1a through which a blood sample can be introduced into blood separating component 11. A blood taking opening 13 is provided in the rear section of the top retaining component 10b which is displayed in FIG. 2a on the right.

FIG. 2b shows the retaining component 10 which encompasses the blood separating component 11 represented by a broken line in the plan view. The first blood separating section 12a can be seen in the front end section of blood separating component 11 shown in FIG. 2b on the left.

Figure 3:
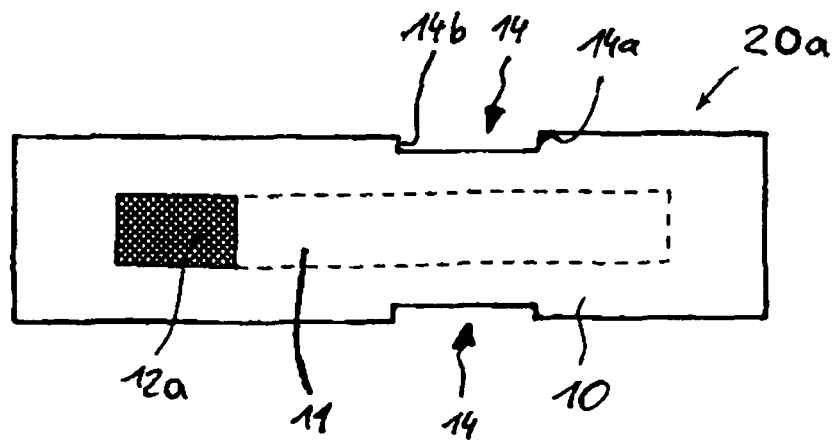
FIG. 3 shows a plan view of a second separating strip under the invention according to an example of embodiment.

FIG. 3 shows a plan view of a second separating strip 20a under the invention.

The second separating strip 20a is distinguished from the first separating strip 2a, as it is shown in both FIG. 2a and 2b, by the provision of rectangular openings 14 with a rear limit stop 14a and a front limit stop 14b on each longitudinal side of the second separating strip 20a. Said limit stops 14a and 14b will mark stops for the nose-shaped lugs 9 in the condition where the separator is inserted so that the second separating strip 20a can move between two defined positions in relation to the separator.

The area called the first blood introducing section 12a in both FIG. 2 and FIG. 3 of separating strip 1a or 20a respectively can also be called a separation field. Each of the separating strips 2a and 20a bears a serial number on its underside which is not visible in FIG. 2 and FIG. 3.

Figure 4:
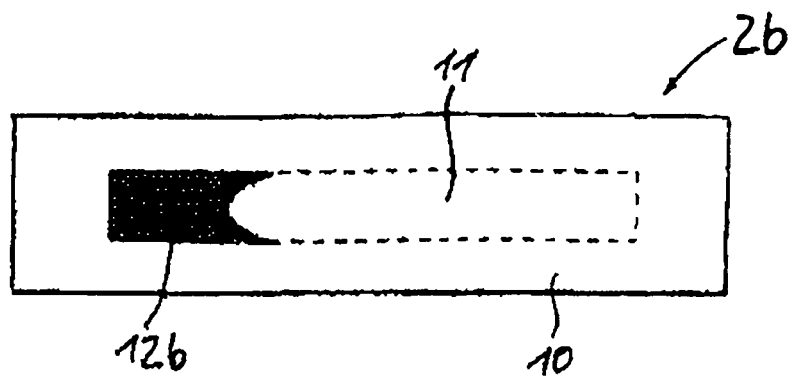
FIG. 4 shows a plan view of a third separating strip under the invention according to an example of embodiment.
Figure 5:
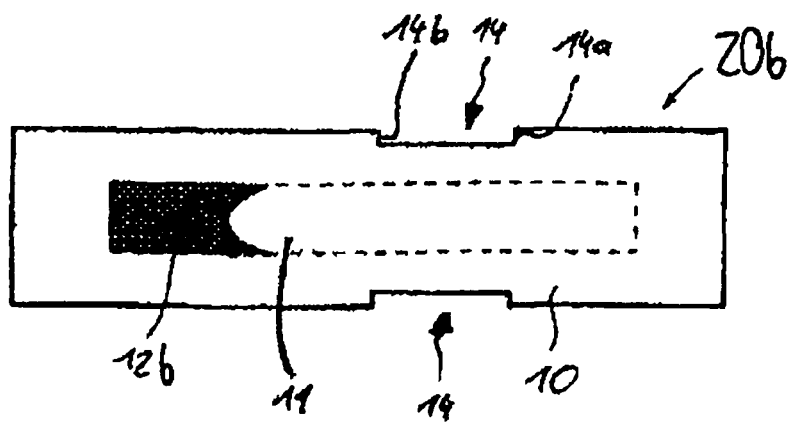
FIG. 5 shows a plan view of a fourth separating strip under the invention according to an example of embodiment.

FIG. 4 shows a plan view of a third separating strip 2b, and FIG. 5 shows a plan view of a fourth separating strip 20b.

The third separating strip 2b and the fourth separating strip 20b are only distinguished from the first separating strip 2a and the second separating strip 20a by their blood introducing section 12b whose rear side is designed as a semicircle.

Figure 6:
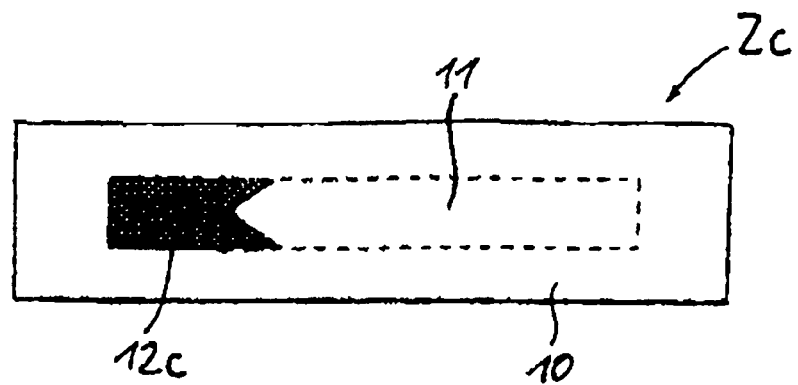
FIG. 6 shows a plan view of a fifth separating strip under the invention according to an example of embodiment.
Figure 7:
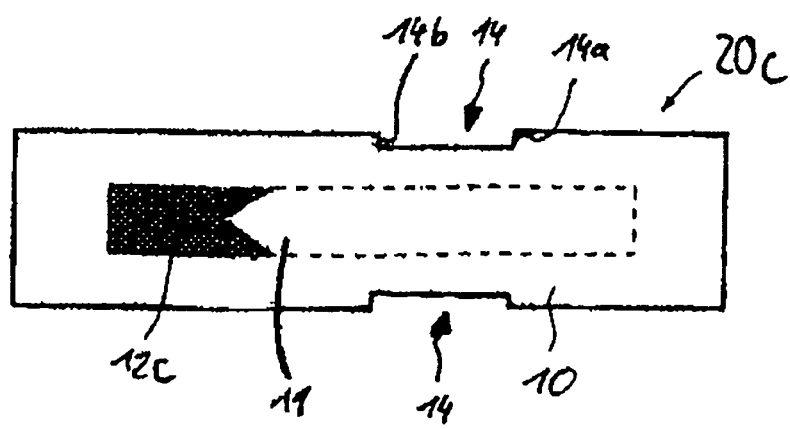
FIG. 7 shows a plan view of a sixth separating strip under the invention according to an example of embodiment.

FIG. 6 shows a plan view of a fifth separating strip 2c, and FIG. 7 shows a plan view of a sixth separating strip 20c.

The fifth separating strip 2c and the sixth separating strip 20c are only distinguished from the first separating strip 2a and from the second separating strip 20a by their blood introducing section 12c which is shaped like a V on its rear side.

Figure 8:
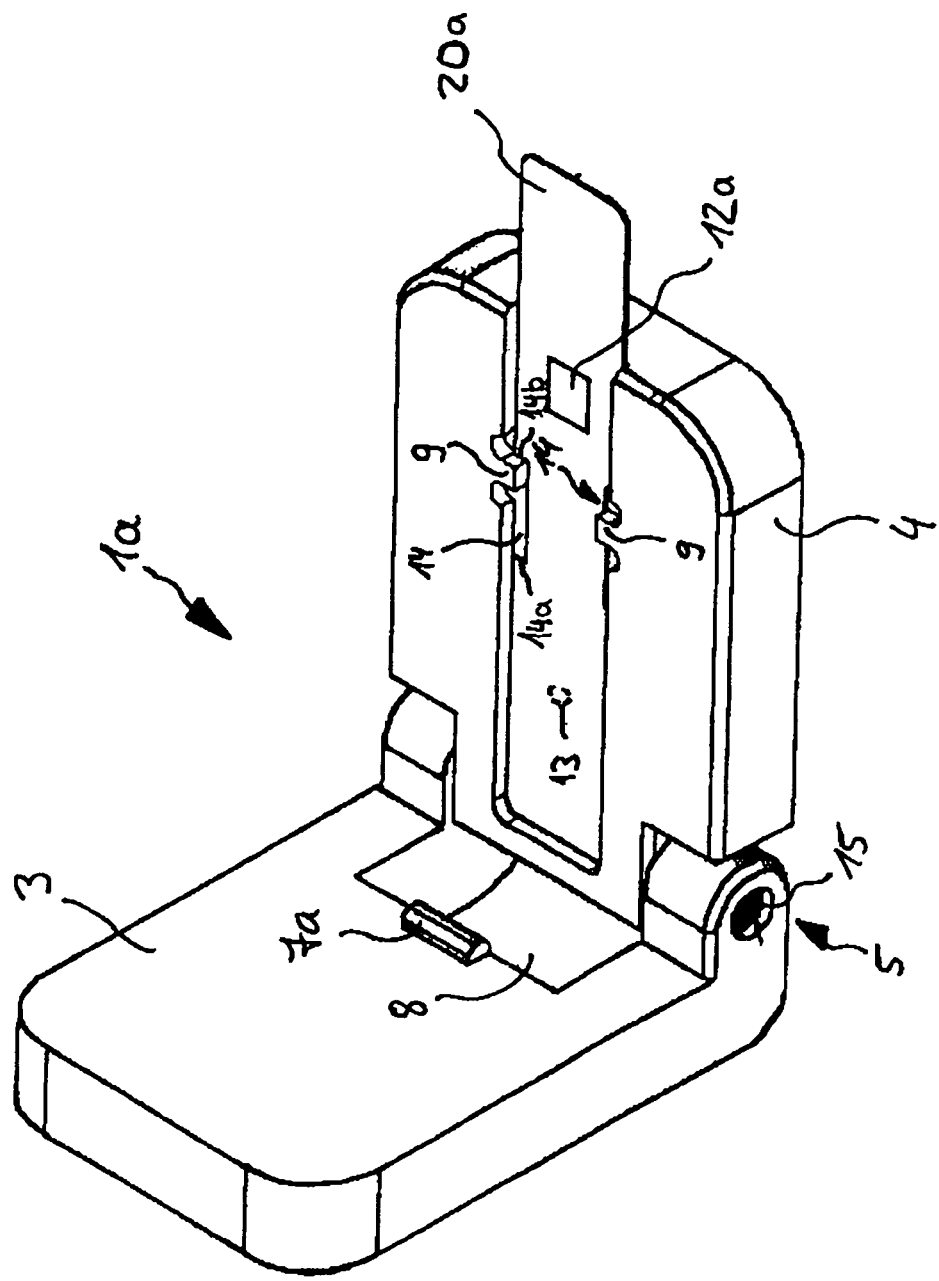
FIG. 8 shows an exploded view of the first separator of FIG. 1a in its folded-open condition into which the separating strip of FIG. 3 is inserted.

FIG. 8 shows an exploded view of the first separator 1a with inserted second separating strip 20a in its unfolded condition.

The first blood introducing section 12a can be seen on the top of the second separating strip 20a. The blood taking opening 13 which is also arranged on the top of the second separating strip 20a is marked with a broken line at the rear end of the second separating strip 20a displayed in FIG. 8 on the left. The second nose 7b provided in the indentation 6 can therefore not be seen in FIG. 4 as it is covered by the second separating strip 20a.

As can be seen in FIG. 8, the front limit stops 14b of openings 14 of the second separating strip 20a are in contact with the nose-shaped lugs 9 and that the second separating strip 20a is thus in its pushed-in position.

Figure 9B:
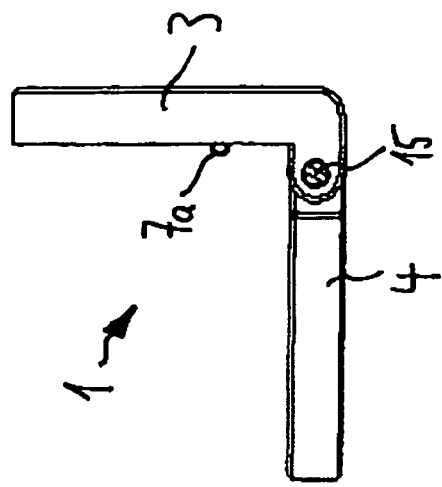
FIG. 9b shows a sectional view of the first separator of FIG. 1a in its folded-open condition.
Figure 9A:
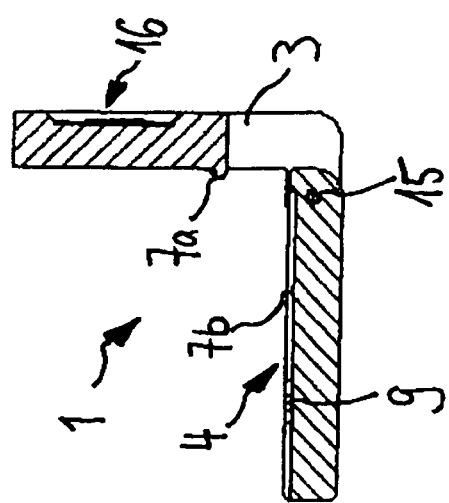
FIG. 9a shows a side view of the first separator of FIG. 1a in its folded-open condition.

FIG. 9a shows an exploded view of a longitudinal section of the first separator 1a in its unfolded condition.

In the upper part, the perpendicular arranged top part 3 can be seen which is linked in a pivoting way through pivot pin 15 to the bottom part 4 which is arranged horizontally in FIG. 9a. An opening 16 is located at the top side of top part 3 which faces the rear, and this opening bears a type designation or a company logo, for instance. At the underside of top part 3 the first nose 7a can be seen facing the front. On the top of bottom part 4 both the nose-shaped lug 9 provided on the side walls of the indentation and the second nose 7b provided can be seen at the underside of indentation 6.

FIG. 9b shows a side view of the first separator 1a in its folded-open condition.

Here, the horizontal bottom part 4 and the top part 3 which is perpendicular to it can be recognized. The first nose 7a arranged at the underside of top part 3 can be seen.

FIG. 10 shows an exploded view of pivot pin 15.

The pivot pin 15 consists of a head 18 with a front 19 which is provided with a slot 20 into which a screwdriver may engage thus moving or rotating the pivot pin 15. The latter also has a bolt 17 with a diameter lower than the head 18 and kept at a distance from head 18 by means of notch 21. In FIG. 10 the bolt 17 is foreshortened. In practice, the bolt is so long that it extends from the head 18 through bottom part 4 to the opposite joint section of top part 3.

The separator 1a, 1b, 1c, 1d, 1e and 1f including the second separating strip 20a is operated as follows:

A blood sample of approx. 50 µl is applied to the first blood introducing section 12a with a pipette, for instance. Capillary forces will separate the blood serum or blood plasma from the erythrocytes in such a way that the blood serum or blood plasma will collect next to the blood taking opening 13 at the rear end of blood separating component 11.

The next drawing as per FIG. 8 shows the second separating strip 20a with its first blood introducing section 12a facing upwards and inserted in the separator 1a, 1b, 1c, 1d, 1e and 1f in such a way that the front limit stops 14b will stop at the nose-shaped lugs 9. The second separating strip 20a is therefore in its pushed-in condition.

After expiry of a period of approx. 0.5 to 2 minutes, depending on the analyte, the top part 3 and bottom part 4 are folded together, thus closing the separator. The top part 3 and bottom part 4 are maintained in a slightly compressed position, at the same time carefully pulling the second separating strip 20a back until the rear limit stops 14a make contact with the nose-shaped lugs 9. If the fifth separators 1e are used with permanent magnets 22, manual compression of top part 3 and bottom part 4 can be omitted as top part 3 and bottom part 4 are pressed against each other by magnetic force.

The action of noses 7a and 7b on the blood separating component 11 has the result that the blood serum or blood plasma is pressed out of blood taking opening 13 and escapes at the tip of the second separating strip 20a.

If the second separator 1b, the third separator 1c or the sixth separator 1f are used, the noses 27a and 27b with their semicircle shapes or the V-shaped noses 37a and 37b or 38a and 38b respectively will have the result that blood serum or blood plasma is concentrated in the central area of the second separating strip 20a and pressed out of the second separating strip 20a in a centerline position when the second separating strip 20a is pulled out of the indentation 6.

If the fourth separator 1d are used, the rollers 47a and 47b will achieve the effect of pressing the blood serum or blood plasma out of the second separating strip 20a in a particularly careful way when the second separating strip 20a is pulled out of the indentation 6.

If a fourth separating strip 20b with a semicircular blood inserting section 12b or a sixth separating strip 20c with a V-shaped blood inserting section 12c is used, instead of the second separating strip 20a, the blood serum or blood plasma will be even better concentrated and pressed out in the central area of blood inserting sections 12b and 12c.

The blood serum or blood plasma can now be taken through the opening 62 without touching, by sucking it with a capillary bulb, for instance. Finally, the capillary bulb will have to be sealed using a sealing kit to prevent the blood serum or blood plasma from flowing out. The capillary bulb is now ready for measurement.

FIG. 11 shows an exploded view of a sixth separator 50 including a bottom part 52 and a top part 60 removed from it.

The bottom part 52 and top part 60 have identical thicknesses and have an approximate rectangular form with rounded corners, the central area of the rear end of top part 60 having a rectangular opening 62. The side areas of bottom part 52 are provided with two oblong guide bars 58 which are designed as longitudinal openings in FIG. 11. The top of bottom part 52 has an oblong indentation 54 which is running across the top of bottom part 52 from the front to the rear, limited by side walls on the rear and to the left and right, and open to the front. The rear side wall may also have an opening in order to allow better taking of separated blood serum or blood plasma.

On the left and right side walls of indentation 54, there are fixation noses 56 opposed to each other in a front area, the width of each of the nose equalling the width of the openings 14 of separating strips 20a, 20b and 20c. These fixation noses 56 are used to reliably fix and retain in position a separating strip 20a, 20b, 20c inserted into indentation 54.

Figure 12:
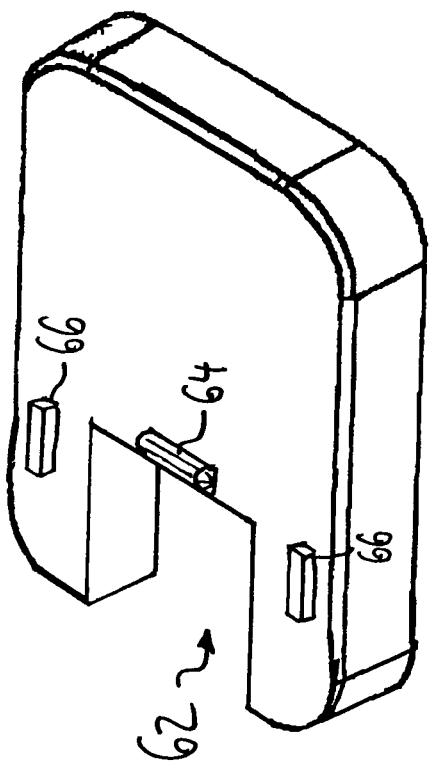
FIG. 12 shows an exploded view of the top part in FIG. 11 seen from an oblique angle from below.

FIG. 12 shows an exploded view of the top part 60 seen from an oblique angle from below.

Just in front of the rectangular opening 62 at the rear of top part 60, there is a roller 64 which is mounted on bearings and can rotate around an axle arranged approximately at the height of the underside of top part 60 and which is vertical to the longitudinal direction of the indentation 54 or the moving direction of the separating strip. The roller 64 therefore protrudes a little downwards out of the underside of top part 60 so that the roller 64 starts to roll once the separating strip fulfils a shifting motion, thus pressing the blood serum or blood plasma off the separating strip because of the pressure effect on the separating strip.

Two gliders 66 protrude downwards beyond the surface of top part 60 in the lateral areas of the top part 60 next to the opening 62. These gliders 66 can be placed into the guide bars 58 of the bottom part 52, thus guiding the top part 60 in the guide bars 58 during the shifting motion. In relation to the longitudinal direction of the sixth separator 50, the gliders 66 are arranged behind the roller 64 so that the rear ends of guide bars 58 mark a stop for them and the shifting motion of the top part 60 is limited to the rear, the roller 64 thus pressing the blood serum or blood plasma out of the blood taking opening 13, but not being able to touch the blood serum or blood plasma pressed out in the rear section of separating strip 20a, 20b, 20c.

The gliders 66 belonging to the top part and the guide bars 58 belonging to the bottom part therefore combine to form a shifting mechanism which can be used to shift the top part 60 against the bottom part 52.

Figure 13:
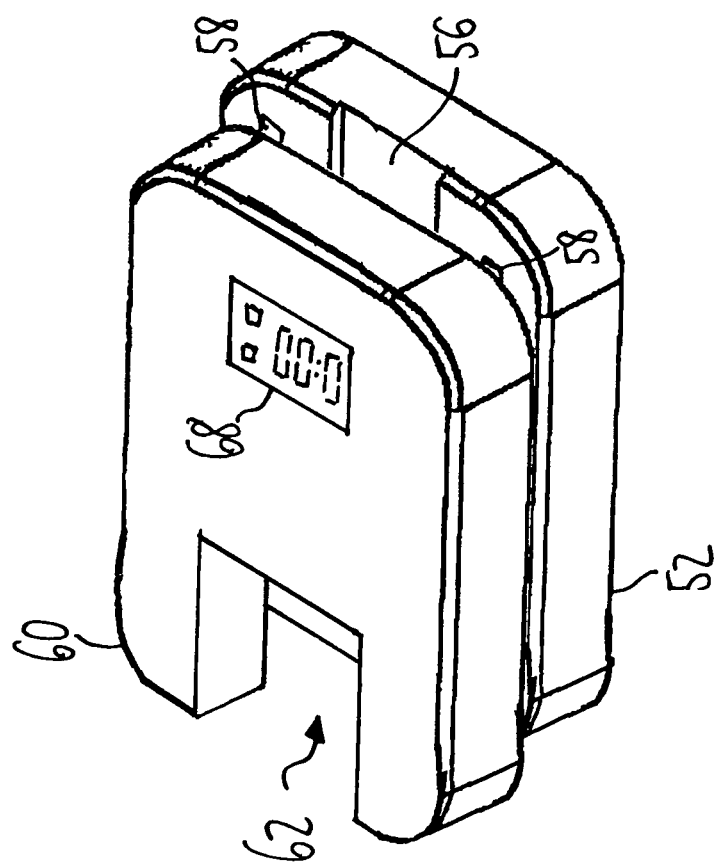
FIG. 13 shows an exploded view of the seventh separator with the top part placed on the bottom part in a maximum shifting position.

Said shifting mechanism is included in FIGS. 11 through 13 as an example and can be designed in any way imaginable. Guide bars can be provided in the side areas of bottom part 52, for instance, and the top part 60 may be wider than the bottom part 52 and have gliders which engage into the lateral guide bars of the bottom part 52, for instance. In this case, the top part 60 can be shifted against the bottom part 52 to the rear until the indentation 54 is uncovered and the separating strip 20a, 20b, 20c can be inserted. As in the embodiment described in FIGS. 11 through 13, the gliders may be arranged in relation to the longitudinal direction so that the rear ends of the lateral guide bars mark a stop for them and the shifting motion of the top part 60 is limited to the rear, the roller 64 thus pressing the blood serum or blood plasma out of the blood taking opening 13, but not being able to touch the blood serum or blood plasma pressed out in the rear section of separating strip 20a, 20b, 20c.

FIG. 13 shows an exploded view of the sixth separator 50 including the top part 60 placed on the bottom part 52 in a maximum shifting position.

In this case, which is not visible in FIG. 13, the gliders 66 have made contact with the rear ends of guide bars 58, and the rear end of top part 60 is protruding beyond that of bottom part 52.

Moreover, a chronometer unit 68 with a digital display and two control keys, corresponding to the chronometer unit 48 of the first separator 1a, is arranged in a front area on the top of top part 60.

The sixth separator 50 with separating strip 20a, 20b, 20c is operated as follows:

The separating strip 20a, 20b, 20c is inserted into the separator 50, with the first blood inserting section 12a facing upwards, so that the fixation noses 56 will engage into opening 14 and the separating strip 20a, 20b, 20c is fixed against the bottom part 52 and retained in this position. A blood sample of approx. 50 μl blood is applied to the first blood introducing section 12a, 12b, 12c with a pipette, for instance, and capillary forces will separate the blood serum or blood plasma from the erythrocytes in such a way that the blood serum or blood plasma will collect next to the blood-taking opening 13 at the rear end of blood separating component 11. The top part 60 is now placed on to the bottom part 52 to align with it so that the gliders 66 are located in the guide bars 58. The chronometer unit 68 is started now either by pressing a control key or by a switch or sensor, which detects the moment when the top part 60 is placed on the bottom part 52. The chronometer unit will emit an acoustic or optical signal after expiry of the specified period. The top part 60 is now shifted against the bottom part 52 manually or motor-driven by means of an integrated electrical motor to the rear until the gliders 66 make contact with the ends of guide bars 58. The action of roller 64 on the blood separating component 11 causes the blood serum or blood plasma to be pressed out of the blood taking opening 13 and escape at the tip of separating strip 20a, 20b, 20c.

The blood serum or blood plasma can now be taken through the opening 62 of the top part 60, by sucking it with a capillary bulb, for instance. Finally, the capillary bulb will have to be sealed using a sealing kit to prevent the blood serum or blood plasma from flowing out. The capillary bulb is now ready for measurement.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A separator for the taking of blood serum or blood plasma of a blood sample from a separating strip comprising:
    a bottom part and a top part which can be moved in relation to the bottom part; and
    wherein an oblong indentation is provided on the top side of bottom part to support the separating strip, this indentation being limited by side walls on at least two opposite sides, each of the side walls being provided with at least one nose-shaped lug to fix the separating strip inserted into the indentation, said lug protruding into the indentation on the side; and
    wherein at least one nose is provided on at least one of the top of the bottom part or on the base of top part to exert a defined local pressure on the separating strip, thus pressing blood serum or blood plasma out of the rear end of the separating strip whenever top part is moved in relation to the bottom part; and
    wherein two gliders protrude from top part and the bottom part is provided with two guide bars to support the gliders to guide the top part during relative motion.

2. The separator according to claim 1, characterized in that the separating strip can be pushed into the indentation and pulled out of the indentation.

3. The separator according to claim 1, characterized in that the at least one nose is provided at the indentation, in particular at the base of the indentation.

4. The separator according to claim 1, characterized in that a first nose is provided on the underside of top part and a second nose is provided on the base of indentation.

5. The separator according to claim 1, characterized in that the at least one nose is shaped like a barrier.

6. The separator according to claim 1, characterized in that the at least one nose is provided transversally to the longitudinal direction of the indentation.

7. The separator according to claim 1, characterized in that at least one nose is shaped like a bow.

8. The separator according to claim 1, characterized in that at least one nose is shaped like two legs arranged like an arrow.

9. The separator according to claim 1, characterized in that at least one nose is shaped like a roller or roll which rotates around an axle inserted in the top part and/or the bottom part.

10. The separator according to claim 1, characterized in that at least one nose is made from an elastic material, in particular from rubber.

11. The separator according to claim 1, characterized in that at least one nose is designed as an elastic metal tongue.

12. The separator according to claim 1, characterized in that the nose is a roller.

13. The separator according to claim 12, characterized in that a drive motor is provided for the roller.

14. The separator according to claim 1, characterized in that the top part has an opening arranged in such a manner to allow access to the blood serum or blood plasma emerged from the rear end of the separating strip.

15. The separator according to claim 1, characterized in that a chronometer unit is provided in the top part or bottom part which measures a specified period, emitting an optical or acoustical signal after expiry of this period.

16. The separator according to claim 1, characterized in that a chronometer unit is provided in the top part or bottom part which measures a specified period, emitting an optical or acoustical signal after expiry of this period.

17. A separating strip for the separation of blood serum or blood plasma of a blood sample by means of a separator, comprising:
    a blood separating component,
    a retaining component to cover and retain the blood separating component,
    a blood introducing section provided in a section of retaining component which covers the front end of the blood separating component, and
    a blood taking opening provided in a section of retaining component which covers the rear end of the blood separating component,
    wherein the separating strip has at least one narrow on at least one longitudinal side including a rear and a front limit stop so that the separating strip can be moved across the distance defined by the limit stops.

18. The separating strip according to claim 17, characterized in that the blood sample can be introduced into the blood separating component through the blood inserting section and the blood separating component is constituted so that the introduced blood sample can be separated by capillary action so that the blood serum or blood plasma collect in the rear end of the blood separating component and the erythrocytes collect in the front end of the blood separating component.

19. The separating strip according to claim 17, characterized in that at least one narrow has a rectangular shape.

20. The separating strip according to claim 17, characterized in that the separating strip is shaped like a semicircle or V on one side.

* * * * *